United States Patent
Wen et al.

(10) Patent No.: US 10,100,351 B2
(45) Date of Patent: Oct. 16, 2018

(54) HIGH-THROUGHPUT SEQUENCING DETECTION METHOD FOR METHYLATED CPG ISLANDS

(71) Applicant: PEKING UNIVERSITY, Beijing (CN)

(72) Inventors: Lu Wen, Beijing (CN); Jingyi Li, Beijing (CN); Yanyi Huang, Beijing (CN); Fuchou Tang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 357 days.

(21) Appl. No.: 14/392,322

(22) PCT Filed: Nov. 15, 2013

(86) PCT No.: PCT/CN2013/087231
§ 371 (c)(1),
(2) Date: Dec. 24, 2015

(87) PCT Pub. No.: WO2014/205981
PCT Pub. Date: Dec. 31, 2014

(65) Prior Publication Data
US 2016/0298183 A1    Oct. 13, 2016

(30) Foreign Application Priority Data

Jun. 27, 2013 (CN) .......................... 2013 1 0259709

(51) Int. Cl.
| C12P 19/34 | (2006.01) |
| C12Q 1/6858 | (2018.01) |
| C12Q 1/6827 | (2018.01) |
| C12Q 1/6855 | (2018.01) |
| C12Q 1/6874 | (2018.01) |

(52) U.S. Cl.
CPC ......... *C12Q 1/6858* (2013.01); *C12Q 1/6827* (2013.01); *C12Q 1/6855* (2013.01); *C12Q 1/6874* (2013.01)

(58) Field of Classification Search
None
See application file for complete search history.

(56) References Cited

U.S. PATENT DOCUMENTS

| 5,786,146 A | * | 7/1998 | Herman | ............... | C12Q 1/6827 435/6.12 |
| 6,017,704 A | * | 1/2000 | Herman | ............... | C12Q 1/6827 435/6.12 |
| 6,207,372 B1 | * | 3/2001 | Shuber | .................. | C12Q 1/686 435/6.12 |
| 2004/0038245 A1 | * | 2/2004 | Belinsky | ............. | C12Q 1/6827 435/6.12 |
| 2007/0141575 A1 | * | 6/2007 | Han | ...................... | C12Q 1/686 435/6.11 |
| 2010/0092951 A1 | * | 4/2010 | Tetzner | ................ | C12Q 1/6858 435/6.12 |
| 2010/0184153 A1 | * | 7/2010 | Brookes | ................ | C12Q 1/686 435/91.2 |
| 2011/0294689 A1 | * | 12/2011 | Namsaraev | .......... | C12Q 1/6816 506/9 |

FOREIGN PATENT DOCUMENTS

| CN | 101613749 A | 12/2009 |
| CN | 102399861 A | 4/2012 |
| CN | 103103624 A | 5/2013 |

* cited by examiner

*Primary Examiner* — Kenneth R Horlick
(74) *Attorney, Agent, or Firm* — Muncy, Geissler, Olds, Lowe, P.C.

(57) ABSTRACT

A high-throughput sequencing method for detecting methylated CpG islands includes: processing a DNA sample by using a modifier, and converting cytosine in the DNA sample into uracil, and keeping 5'methylcytosine unchanged; amplifying the obtained segment by using a primer A and DNA polymerase, to obtain a segment having one end being capable of anchoring a junction primer C; amplifying the obtained segment by using a primer B and DNA polymerase, to obtain a segment gathering methylated CpG islands and having two ends being capable of separately anchoring junction primers C and D; amplifying the obtained segment at a PCR exponent by using the junction primers C and D and the DNA polymerase, to obtain the amplified product; and separating and purifying the amplified product, to form a high-throughput sequencing library and perform computer sequencing, and data analysis.

20 Claims, 7 Drawing Sheets

Specification includes a Sequence Listing.

SEQUENCE LISTING

<160> NUMBER OF SEQ ID NOS: 20

<210> SEQ ID NO 1
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: any h = a or t or c

<400> SEQUENCE: 1
tctttcccta cacgacgctc ttccgatcth hhhhcgch                        38

<210> SEQ ID NO 2
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: any d = a or t or g

<400> SEQUENCE: 2
tggagttcag acgtgtgctc ttccgatctd dddcgcgcgg                      40

<210> SEQ ID NO 3
<211> LENGTH: 58
<212> TYPE: DNA
<213> ORGANISM: Artificial sequence
<220> FEATURE:
<223> OTHER INFORMATION: Synthetic

<400> SEQUENCE: 3
aatgatacgg cgaccaccga gatctacact ctttccctac acgacgctct tccgatct    58

<210> SEQ ID NO 4
<211> LENGTH: 64
<212> TYPE: DNA
<213> ORGANISM: Artificial sequence
<220> FEATURE:
<223> OTHER INFORMATION: Synthetic

<400> SEQUENCE: 4
caagcagaag acggcatacg agatctgatc gtgactggag ttcagacgtg tgctcttccg   60
atct                                                               64

<210> SEQ ID NO 5
<211> LENGTH: 41
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: any d = a or t or g

<400> SEQUENCE: 5
tggagttcag acgtgtgctc ttccgatctd ddcggcggcg g                     41

<210> SEQ ID NO 6
<211> LENGTH: 38
<212> TYPE: DNA
<213> ORGANISM: Artificial Sequence
<220> FEATURE:

<223> OTHER INFORMATION: Synthetic primer
<220> FEATURE:
<221> NAME/KEY: misc_feature
<223> OTHER INFORMATION: any h = a or t or c

<400> SEQUENCE: 6
tctttcccta cacgacgctc ttccgatctk hhhhhccc         38

<210> SEQ ID NO 7
<211> LENGTH: 39
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: any d = a or t or g
<220> FEATURE:
<221> NAME/KEY: misc_feature
<222> LOCATION: (31)..(31)
<223> OTHER INFORMATION: n is a, c, g, or t

<400> SEQUENCE: 7
tggagttcag acgtgtgctc ttccgatctd ndcgcgcgg        39

<210> SEQ ID NO 8
<211> LENGTH: 38
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: any h = a or t or c

<400> SEQUENCE: 8
tctttcccta cacgacgctc ttccgatcth hhcghhch         38

<210> SEQ ID NO 9
<211> LENGTH: 39
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: any d = a or t or g
<220> FEATURE:
<221> NAME/KEY: misc_feature
<223> OTHER INFORMATION: any r = g or a

<400> SEQUENCE: 9
tggagttcag acgtgtgctc ttccgatctd ddcggcggr        39

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(20)

<223> OTHER INFORMATION: n is a, c, g, or t

<400> SEQUENCE: 10
ncgcgcggcg dgcgndgcgn                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(20)
<223> OTHER INFORMATION: any "c" is methylated
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 11
ncgcgcggcg dgcgndgcgn                                                    20

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12
duguguggug dgugddgugd                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(20)
<223> OTHER INFORMATION: any "c" is methylated

<400> SEQUENCE: 13
dcgcgcggcg dgcgddgcgd                                                    20

<210> SEQ ID NO 14
<211> LENGTH: 13
<212> TYPE: DNA
<213> ORGANISM: Artificial Sequence
<220> FEATURE:
<223> OTHER INFORMATION: Synthetic

<400> SEQUENCE: 14
hhhhhcgchc cgh                                                           13

<210> SEQ ID NO 15
<211> LENGTH: 19
<212> TYPE: DNA
<213> ORGANISM: Artificial Sequence

```
<220> FEATURE:
<223> OTHER INFORMATION: Synthetic

<400> SEQUENCE: 15
hhhhhcgchc gccgcgcgh                                                      19

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
hhhhhcgchh cgchcgccgc gcgh                                                24

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
ddddcgcgcg gcgdgcgddd d                                                   21

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
ddddcgcgcg gcgdgcgddg cgdddd                                              26

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
hhhhcgchcg ccgcgcghhh h                                                   21

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20
hhhhcgchhc gchcgccgcg cghhhh                                              26
```

HIGH-THROUGHPUT SEQUENCING DETECTION METHOD FOR METHYLATED CPG ISLANDS

BACKGROUND OF THE INVENTION

Field of the Invention

The present invention relates to detection of methylated CpG islands in a genome using high-throughput sequencing.

Description of Related Art

DNA methylation is the modification of the cytosine (C) to the 5'-methylated-cytosine (5mC) by adding a methyl group to the C5 position of the cytosine. It plays important roles in many biological processes, including regulation of transcription, repression of transposon, genomic imprinting and X-chromosome inactivation, and is a hot topic in the field of molecular biology. In vertebrates including human, DNA methylation mainly occurs at the CpG site (CpG indicates dinucleotide of which the guanine (G) base immediately follows the cytosine base along the DNA strand). The average content of CpG dinucleotides in the vertebrate genome is lower than their expected frequency. However, in some region of the genome, CpG dinucleotides show the expected or even higher frequency and these regions are referred to as CpG islands. CpG islands are mainly found in gene promoters. In the human genome, there are about 30,000 CpG islands, with more than 50% of CpG islands being located in promotes and more than 60% of promoters contain a CpG island. Methylation of the promoter CpG islands leads to silencing of gene expression; this mechanism participates in many biological processes, including X-chromosome inactivation, genomic imprinting, differentiation of embryonic stem cells, development of germ cells, as well as initiation and progressing of cancers. Intragenic and intergenic CpG islands may be unidentified promoters. Comprehensive understanding the biological functions of CpG islands methylation requires systematic and high-efficient techniques.

Traditional techniques for detecting DNA methylation, including restriction enzyme digestion, restriction enzyme digestion and PCR, methylation-specific PCR, can only detect single or a small number of sites. With the progresses in the high-throughput sequencing technologies in recent years, researchers begin to systematically profile DNA methylation at the level of whole genome. The current techniques for detecting DNA methylation using high-throughput sequencing including: 1) methylated DNA immuoprecipitation; 2) methylated CpG immuoprecipitation, and 3) bisulfite sequencing. The former two techniques capture methylated DNA by using an antibody or a recombinant methylated CpG binding protein, followed by high-throughput sequencing; they can only measure the DNA methylation status in a semi-quantitative manner and has a resolution of about 100 base-pair (bp). The bisulfite sequencing is based on the fact that sodium bisulfite treatment converts unmethylated cytosines (C) to uracils (U) whereas methylated cytosines (5mC) are not affected; DNA methylation status thus can be acquired by subsequent high-throughput sequencing. This technique, which is the gold standard of DNA methylation analysis, has a resolution as accurate as a single base pair. In 2009, scientists reported the first human whole-genome DNA methylation map at single-base-pair resolution by using the bisulfite sequencing. However, since this technique sequences the whole genome, the cost is very high, which hampers its application to a large number of samples. The reduced representation bisulfite sequencing technique has been developed (Gu H, et al. Preparation of reduced representation bisulfite sequencing libraries for genome-scale DNA methylation profiling. Nat Protoc. 2011 6(4):468-81.). This method enriches genomic regions of promoters and the CpG islands by means of MspI enzyme digestion, followed by end-repair, A tailing, adapter ligation, size selection and PCR amplification to obtain the library. Though it is more cost-effective than the whole-genome bisulfite sequencing, the process of library establishment is complex and requires five to six days. In addition, the enrichment process is not able to distinguish between the methylated and unmethylated CpG islands, which increase sequencing cost. Another method (patent: methods and application for establishing library of high-throughput sequencing, CN103103624A) captures genomic regions including the CpG islands by using specific probes and then performs bisulfite sequencing. However, the process for capturing and library establishment is rather time-consuming.

Therefore, techniques for high-efficient detection of the methylated CpG islands remain limited.

SUMMARY OF THE INVENTION

The present invention enriches and amplifies the methylated CpG islands from a bisulfite-converted genomic DNA sample by means of a high-CpG-density oligonucleotide primer, simultaneously anchoring the adapter sequences to the amplicons for amplification and then sequencing via a three-steps PCR reaction. This technique allows for highly efficient enrichment of the methylated CpG islands and rapid establishment of the high-throughput sequencing library, representing a novel, high-efficient and cost-effective method for detecting the methylated CpG islands using high-throughput sequencing.

In a first aspect, the present invention provides a method for detecting the methylated CpG islands using the high-throughput sequencing, comprising the following steps:

(a) Treating a DNA sample with a modifying agent to form the modified DNA wherein cytosine bases but not 5'-methyl-cytosine bases of the DNA sample are modified to uracil bases.

The DNA sample can be any suitable DNA polymer. Preferably, the DNA sample is the genomic DNA of animals, plants or microorganisms; more preferably the DNA sample is the genomic DNA of human or mouse.

The DNA sample can derive from human cells, tissues, blood, body fluid, urine, excrement or their combination. In one preferred embodiment, the DNA sample is the cell-free DNA of human plasma or serum. Optionally, the DNA sample can also be the genomic DNA of human whole blood cells or human cancer cell lines.

The agent for treating the DNA sample modifies cytosine bases but not 5'-methyl-cytosine bases under conditions to form single-stranded DNA. The modifying agent can be selected from bisulfite, acetate or citrate. Preferably, the agent is bisulfite. Optionally, bisulfite treatment of the DNA sample can be achieved by using commercial kits such as MethylCode Bisulfite Conversion Kit (Invitrogen) EZ DNA methylation-Gold Kit (ZYMO) or EpiTect Bisulfite Kit (Qiagen).

(b) Providing Primer A and DNA polymerase to the modified DNA to allow at least one round of linear amplification to form the semi-amplicon capable of anchoring Adapter Primer C at one end.

The primer A is composed of a 3' portion and a 5' portion, wherein the 3' portion contains 4 or more nucleotides capable of binding to the modified DNA and allowing amplification. Preferably, the 3' portion contains only C, A and T except for the CpG dinucleotide. More preferably, the second nucleotide at the 3' terminal is C. Preferably, the 3' portion allows preliminary enrichment of the methylated CpG islands, thereby forming the semi-amplicon enriched with the methylated CpG islands and capable of anchoring Adapter Primer C at one end in step (b). The preliminary enriching process, while still need further enriching process in step (c), can increase the net efficiency for enrichment of the methylated CpG islands. To achieve the preliminary enrichment, the 3' portion of primer A needs to contain a certain density of CpG or C. Preferably, the 3' portion of primer A is a moderate-CpG-density sequence of which the 3'-terminal 7 nucleotides contain 1 CpG dinucleotide; alternatively, the 3' portion of primer A is a high-C-density sequence of which the 3'-terminal 5 nucleotides contain 3 or more C, preferably all the 3'-terminal 3 nucleotides are C. Optionally the 3' portion of primer A is a high-CpG-density sequence of which the 3'-terminal 7 nucleotides contain 2 or 3 CpG dinucleotides, here further enriching process in step (c) is not indispensible (see below).

The 5' portion of primer A is used to anchor Adapter Primer C; it allows Adapter Primer C to bind to its reverse complementary sequence for PCR amplification. The word "anchor" is to describe the function of the 5' portion to join Adapter Primer C to the amplicon via PCR. Preferably, the sequences of the 5'-terminal 15 to 40 nucleotides of Prime A are the same as that of the 3'-terminal 15 to 40 nucleotides of Adapter Primer C.

The DNA polymerase can be any suitable polymerase, such as Taq polymerase, ExTaq polymerase, LATaq polymerase, AmpliTaq polymerase, Amplitaq Gold polymerase, Titanium Taq polymerase, KlenTaq polymerase, Platinum Taq polymerase, Accuprime Taq polymerase, Pyrobest DNA polymerase, Pfu polymerase, Pfu polymerase turbo, Phusion polymerase, Pwo polymerase, Vent polymerase, Vent Exo-polymerase, Sequenase™ polymerase, 9° Nm DNA polymerase, Therminator DNA polymerase, Expand DNA polymerase, rTth DNA polymerase, DyNazyme™ EXT polymerase, DNA polymerase I, T7 DNA polymerase, T4 DNA polymerase, Bst DNA polymerase, phi-29 DNA polymerase, and Klenow fragment.

Preferably, the DNA polymerase is capable of strand displacement. It can be any suitable polymerase with the strand displacement activity, including but not restricted to DNA polymerase I (Klenow) large fragment (New England Biolabs (NEB) catelog: M0210S), Klenow fragment (exo-) (NEB catalogue: M0212S), Bst DNA polymerase large fragment (NEB catelog: M0275S), Vent(exo-) (NEB cateloge: M0257S), Deep Vent (exo-) (NEB cateloge: M0259S), M-MulV reverse transcriptase (NEB cateloge: M0253S), 9° Nm DNA polymerase (NEB cateloge: M0260S) and Phi-29 DNA polymerase (NEB cateloge: M0269S). In one preferred embodiment, the DNA polymerase is Klenow fragment (exo-).

Preferably, the DNA polymerase is deficient of exonuclease activity.

Linear amplification refers to that the amount of amplified product increases in a linear instead of an exponential relationship to the amplification times. The step needs at least one round of linear amplification; preferably, 2-30 rounds of linear amplification are performed.

(c) Amplifying the semi-amplicon by using Primer B and DNA polymerase to form the full-amplicon enriched with methylated CpG islands and capable of anchoring Adapter Primer C at one end and Adapter Primer D at the other end;

Primer B is composed of a 3' portion and a 5' portion. The 3' portion contains 7 or more nucleotides and is a high-CpG-density sequence capable of binding to the semi-amplicon and allowing amplification and enrichment of the methylated CpG islands, wherein the high-CpG-density sequence is a sequence of which the 3'-terminal 7 nucleotides contain 2 or 3 CpG dinucleotides. Preferably, the 3' portion of Primer B contains only A and T except for the CpG dinucleotides.

Enrichment of the methylated CpG islands is due to the preference of Primer B to binding to the methylated CpG islands, while not binding to the regions outside the methylated CpG islands, in a genome. This preference is determined by the high-CpG-density nature of the 3' portion of the primer. Our bioinformatics analysis demonstrates that the high-CpG-density sequences are not randomly distributed in the genome, but accumulate at the CpG islands to a certain degree. Hence, a high-CpG-density primer is capable of enriching the methylated CpG islands. Preferably, the 3' portion is also a high-GC-content sequence, which indicates that the total number of C and G bases within the 3'-terminal 10 nucleotides of the primer is equal to or greater than 7. A high-GC-content sequence will not only more accumulate in the CpG islands, but also help additionally increasing the annealing temperature of the primer. Technical personnel in this field can understand that the annealing temperature of a primer is positively correlated with its GC content. The according high-GC-content feature of the primer makes its annealing temperature reaching about 40 to 60 centigrade, thus facilitating binding of the primer to the template and increasing the amplification efficiency. Preferably, the 3' portion of Primer B is an extremely-high-CpG-density sequence, of which the 3'-terminal 7 nucleotides of the primer contains 3 CpG dinucleotides.

The 5' portion of Primer B is used to anchor Primer D. it allows Adapter Primer D to bind to its reverse complementary sequence for PCR amplification. The word "anchor" is to describe the function of the 5' portion to join Adapter Primer D to the amplicon via PCR. Preferably, the sequence of the 5' portion of Primer B is the same as the 3'-terminal 15 to 40 nucleotides of Primer D.

The polymerase can be any suitable polymerase mentioned before. Preferably, the polymerase is hot-start. Preferably, the annealing temperature of the reaction is between about 40 and 60 centigrade.

When the 3' portion of Primer A has a character of high-CpG-density, the semi-amplicons in the step (c) have already enriched the methylated CpG islands (and been able to anchor Adapter Primer C at one end). Thus, the full-amplicons, which enrich the methylated CpG islands and are able to anchor Adapter primer C at one end and Adapter primer D at the other ends, can be obtained by means of Primer B whose 3' portion is just able to bind and amplify the semi-amplicons without a further function of CpG island enrichment.

(d) Amplifying the full-amplicon by using Adapter Primer C, Adapter Primer D and DNA polymerase to form the final-amplicon via PCR exponential amplification.

The word "Adapter Primer" herein refers to that the function of the primer is similar to the "adapter" used in conventional methods for establishing the high-throughput sequencing library (such as Illunnia's TruSeq DNA Sample Prep Kit and Applied Biosystems (ABI)'s The SOLiD™ Fragment Library Construction Kit), which allows binding of the DNA fragments to the flow cell for subsequent amplification and sequencing. Different from the usage of ligation reaction to add "adapter" in conventional methods for establishing high-throughput sequencing library, the present invention adds "adapters" to each end of the amplicons by means of PCR reaction via the anchor sequences at the 5' portion of Primers A and B. Technical personnel in this field can understand that either Primer C or Primer D can contain "barcode" sequences, which facilitate to simultaneously sequence multiple libraries in one flow cell. The Primer C and D correspond to the adapter sequences of a given high-throughput sequencing platform, which includes, but does not limited to, the Illumina's Genome Analyzer IIx, HiSeq and MiSeq platforms, ABI's SoLiD, 5500 W Series Genetic Analyzer and Ion Torrent PGM platforms, and Roche454's GS Junior and GS FLX+ platforms.

(e) Separating and purifying the final-amplicon to form the library for high-throughput sequencing, sequencing the library and analyzing the data.

The approach to separate and purify the final amplicons can be any suitable method, including but not restricted to magnetic beads-based, column-based and gel electrophoresis-based purification. Preferably, the purification method is able to make size-selection for the amplicons. Preferably, the amplicons between 160 and 400 bp are selected. Preferably, the amplicons are separated by using 2% agarose gel electrophoresis and the fragments between 160 and 400 bp are excised and then purified.

The high-throughput sequencing platform for analysis includes, but does not limited to, the Illumina's Genome Analyzer IIx, HiSeq and MiSeq platforms, ABI's SoLiD, 5500 W Series Genetic Analyzer and Ion Torrent PGM platforms, and Roche454's GS Junior and GS FLX+ platforms.

The method for data analysis is not limited and can be any suitable software for data analysis and sequence alignment, which includes, but does not limited to Bismark, BSMAP, Bowtie and SOAP.

In a second aspect, the present invention provides a kit for detecting methylated CpG islands using high-throughput sequencing. The kit comprises a set of primers including the Primer A, Primer B, Adapter Primer C, Adapter Primer D, and the DNA polymerases according to the first aspect, as well as instructions for the kit.

DETAILED DESCRIPTION OF THE PREFERRED EMBODIMENTS

In order that the present invention may be more clearly understood, preferred forms will described with reference to the following examples and drawings. It will be appreciated by persons skilled in the art that numerous variations and/or modification may be made to the invention as shown in the specific embodiments without departing from the spirit or scope of the invention as broadly described.

Figure 1:
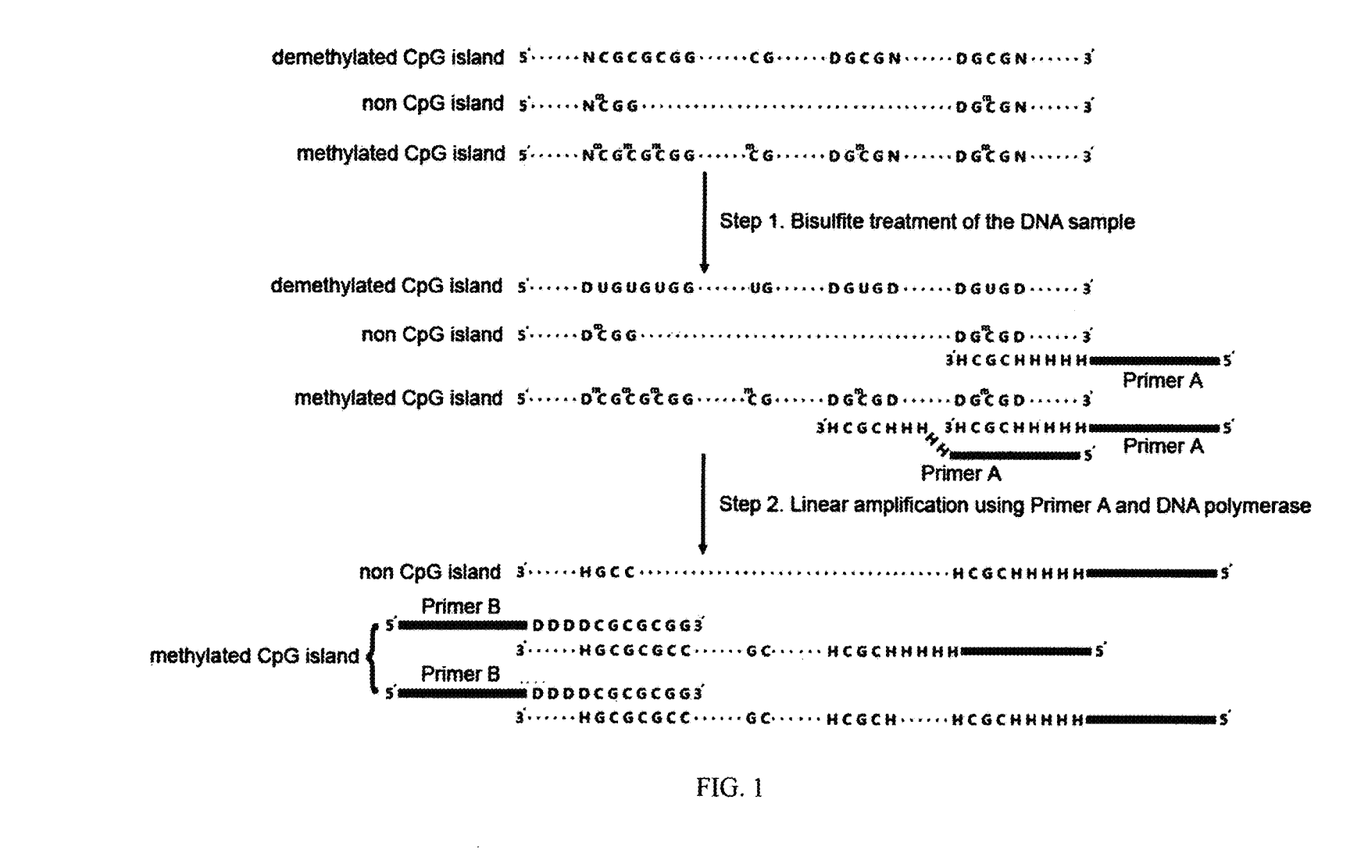
FIG. 1 Schematic of the present invention for detecting methylated CpG islands based on the high-throughput sequencing (SEQ ID NOS: 10-20).

The present invention enriches and amplifies the methylated CpG islands from a bisulfite-converted genomic DNA sample by means of a high-CpG-density oligonucleotide primer, simultaneously anchoring the adapter sequences to the amplicons for high-throughput sequencing via a three-steps PCR reaction. An example of the present invention is shown below (FIG. 1).

1. Bisulfite Conversion of the DNA Sample.

The bisulfite conversion is performed by using the MethylCode™ Bisulfite Conversion Kit (Invitrogen) according to the protocol provided by the manufacturer. Detailed steps are as follows:

1.1 Preparing the CT conversion reagent: Add 900 µl of sterile distilled water, 50 µl of resuspension buffer, and 300 µl of dilution buffer directly to one tube of CT conversion reagent; mix by shaking or intermittent brief vortexing for 10 minutes for dissolvation, keep protected from light at room temperature;

1.2 Add 20 µl of the DNA sample ranging from 500 pg to 500 ng to a PCR tube;

1.3 Add 130 µl of CT conversion reagent to the DNA sample, and mix by flicking the tube or pipetting up and down;

1.4 Place the tube in a thermal cycler and run the following program: 98° C. for 10 minutes, 64° C. for 2.5 hours and 4° C. storage for up to 20 hours;

1.5 Place a spin column in a collection tube and add 600 µl of binding buffer to the column;

1.6 Add the sample from step 1.4 to the binding buffer in the column; close the cap and mix by inverting several times;

1.7 Centrifuge at full speed (≥10,000×g) for 30 seconds, then discard the flow-through;

1.8 Add 100 µl of wash buffer prepared with ethanol to the column, and centrifuge at full speed for 30 seconds; discard the flow-through;

1.9 Add 200 µl of desulphonation buffer to the column and let the column stand at room temperature for 15-20 minutes;

1.10 Centrifuge at full speed for 30 seconds; discard the flow-through;

1.11 Add 100 µl of wash buffer with ethanol to the column and centrifuge at full speed for 30 seconds; discard the flow-through;

1.12 Repeat the wash in step 1.11 one more time, then transfer the spin column to a new, clean 1.5-ml microcentrifuge tube;

1.13 Add 10 µl of elution buffer directly to the column matrix; centrifuge at full speed for 30 seconds to elute the DNA.

2. Lineal Amplification by Means of Primer a and DNA Polymerase.

2.1 Prepare the following reaction mixture in a PCR tube for the DNA sample obtained from step 1.13:

| Contents | Volume |
| --- | --- |
| The DNA sample (from step 1.13) | 4 µl |
| NEBuffer 2 | 1.5 µl |
| dNTP (2.5 mM) | 1.5 µl |
| Primer A (5 uM) * | 1 µl |

| Contents | Volume |
|---|---|
| Water | 6 μl |
| Klenow (exo-) ** | 0.3 μl × 5 (times, see step 2.5) = 1.5 μl |
| Total | 15 μl |

*: Primer A: <u>TCTTTCCCTACACGACGCTCTTCCGATCT</u>HHHHHCGCH (H = A/T/C), the 3' portion of Primer A is underlined by a wave line ' and the 5' portion is underlined by a straight line ' showed as SEQ ID No: 1 in the SEQUENCE LISTING
**: add at step 2.3

2.2 Place the tube in a thermal cycler and run the following program: 95° C. for 2 minutes and 4° C. for storage;

2.3 Add 0.3 μl of Klenow Fragment (exo-) (NEB catalog: M0212S), mix and briefly centrifuge;

2.4 Place the tube in a thermal cycler and run the following program: 4° C. for 50 seconds, 10° C. for 50 seconds, 20° C. for 50 seconds, 30° C. for 50 seconds, 37° C. for 5 minutes, 95° C. for 10 seconds, 4° C. for pause;

2.5 Repeat step 2.3 and 2.4 for a total of 4 times, omit the step of 4° C. for pause at the last time;

2.6 Run the following program to inactivate the Klenow Fragment: 75° C. for 20 minutes and 50° C. for pause.

3. Amplification by Means of Primer B and DNA Polymerase.

3.1 Prepare the following reaction mixture in a new PCR tube:

| Contents | Volume |
|---|---|
| Ex Taq Buffer | 0.5 μl |
| Primer B (10 uM) * | 0.5 μl |
| HS Ex Taq (Takara catalog: DRR006B) | 0.3 μl |
| Water | 3.7 μl |
| Total | 5 μl |

*: Primer B: <u>TGGAGTTCAGACGTGTGCTCTTCCGATCT</u>DDDDCGCGCGG (D = A/T/G); the 3' portion is underlined by a wave line, and the 5' portion is underlined by a straight line 'showed as SEQ ID No: 2 in the SEQUENCE LISTING 3.2 Place the tube in a thermal cycler and preheat to 50° C.;

3.3 Add the preheated mixture to the products (the semi-amplicons) from step 2.6, mix by pipetting up and down 5-6 times;

3.4 Place the tube in a thermal cycler and run the following program: 95° C. for 3 minutes, 50° C. for 1 minutes, 72° C. for 1 minutes, 50° C. for pause.

4. Exponential Amplification Using Adapter Primer C, Adapter Primer D and DNA Polymerase.

4.1 Prepare the following reaction mixture in a new PCR tube:

| Contents | Volume |
|---|---|
| Ex Taq Buffer | 12 μl |
| Adapter Primer C (100 uM) * | 2.4 μl |
| Adapter Primer D (100 uM) ** | 2.4 μl |
| dNTP (2.5 mM) | 12 μl |
| HS Ex Taq (Takara catalog: DRR006B) | 1.2 μl |
| Water | 90.8 μl |
| Total | 120 μl |

*: Adapter Primer C:
AATGATACGGCGACCACCGAGATCTACAC<u>TCTTTCCCTACACGACGCTCTTCCGATCT</u>;
the underlined oligonucleotide sequence is the same as the 5' portion of Primer A ' showed as SEQ ID No: 3 in the SEQUENCE LISTING;
**: Adapter Primer D:
CAAGCAGAAGACGGCATACGAGAT<u>CTGATCGTGAC</u><u>TGGAGTTCAGACGTGTGCTCTTCCGATCT</u>, the underlined (by a straight line) oligonucleotide sequence is the same as the 5' portion of Primer B and the barcode sequence (corresponding to the Illumina index 9) is
underlined by a double-line ' showed as SEQ ID No: 4 in the SEQUENCE LISTING;

4.2 Preheat the mixture at 50° C. in a thermal cycler;

4.3 Add the preheated mixture to the product (full-amplicons) from step 3.4, mix by pipetting up and down 5-6 times;

4.4 Place the tube in a thermal cycler and run the following program: 95° C. for 3 minutes;

4.5 Run the following program: 20 cycles of 95° C. for 30 seconds, 67° C. for 30 seconds, 72° C. for 1 minute, and then 4° C. for storage.

5. Size-Selection, Purification, High Throughput Sequencing and Data Analysis.

5.1 Prepare 2% agarose gel, add 1×SYBR Safe (Invitrogen);

5.2 Run the products (final-amplicons) from step 4.5 in the agarose gel by electrophosis;

5.3 Imagine the gel;

5.4 Excise the gel for DNA fragments ranging from 160 to 400 bp;

5.5 Purify the DNA from the gel by using the QIAquick Gel Extraction Kit (Qiagen) according to the manufacturer's protocol, obtaining the library for high throughput sequencing;

5.6 Analyze the size distribution of the library by using the Bioanalyzer_2100 (Agilent) and quantify the concentration of the library by using QPCR;

5.7 Sequence the library on an Illumina HiSeq2000 sequencer at pair-end 100 bp reads to obtain the raw sequencing data;

5.8 Data analysis: firstly discard whole or any subsets of adapter sequences and low quality reads, then map the reads to the human genome reference (hg19), and then perform subsequent bioinformatics analysis.

Figure 2:
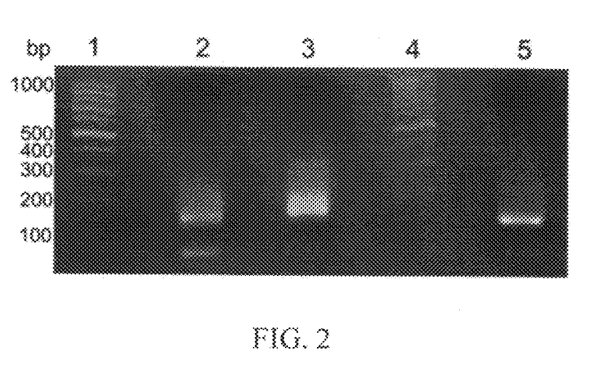
FIG. 2 Agarose gel electrophoresis results of the present invention for amplification of the genomic DNAs extracted from HeLa cells and human peripheral blood mononuclear cells (hPBMCs).

FIG. 2 shows 2% agarose gel electrophosis results of the products amplified from the genomic DNAs of HeLa cells and hPBMCs by using the present invention. Lane 1 and 4 are DNA markers; lane 2 is the result of the HeLa cells from 15 ng of bisulfite-converted DNA; lane 3 is the result of the hPBMCs (from an adult male) from 30 ng of bisulfite-converted DNA; lane 5 is the non-template control. FIG. 2 shows that the genomic DNAs of both the HeLa cells and hPBMCs are positively amplified. These results demonstrate that the present method, which is able to work with as low as 15 ng of genomic DNA as the starting material, is highly efficient and sensitive.

Figure 3:
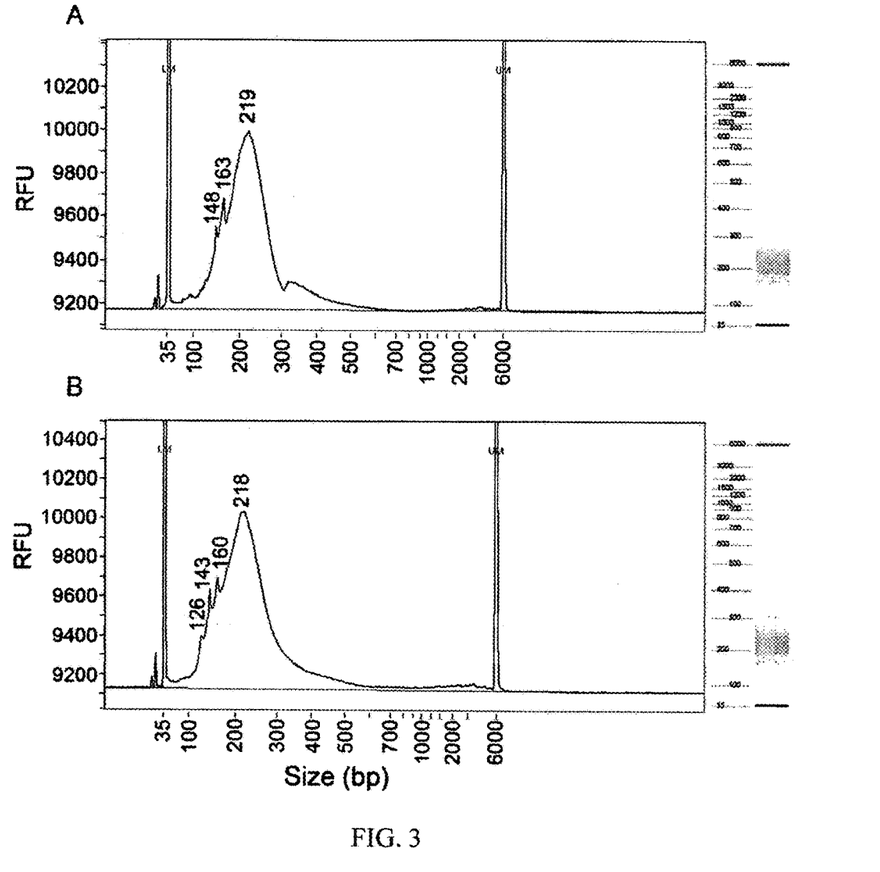
FIG. 3 Bioanalyzer_2100 results showing the size distribution of the libraries established from the genomic DNAs of HeLa cells and hPBMCs by the present invention.

FIG. 3 shows the Bioanalyzer_2100 results of the libraries established from the genomic DNAs of HeLa cells and hPBMCs by using the present invention. The libraries are made from the amplified products mentioned in FIG. 2 by excision and purification of the 2% agarose gel after electrophosis. FIG. 3A show the result of the HeLa cells and FIG. 3B show the result of the hPBMCs. The results show that the fragment size of the libraries ranges from 160 to 280 bp.

The two libraries are sequenced on the HiSeq2000 platform, obtaining 1.3 and 1.5 gigabase (Gb) raw data for the HeLa cells and the hPBMCs, respectively. The statistical analysis of the data is shown in Table 1. The CpG islands comprise about 0.7% of the whole human genome; in contrast, in the sequencing data of the present invention for the HeLa cells and the hPBMCs, 39% and 20% of the reads map to the CpG islands, respectively. Thus, the present invention enriches the CpG islands for 56 and 29 times for the HeLa cells and the hPBMCs, respectively. The present invention achieves an average depth of 20-30× for the genomic regions including the methylated CpG islands by sequencing only 1~2 Gb raw data. In contrast, the whole genome bisulfate sequencing requires 150~200 Gb raw data to achieve a similar depth. This demonstrates that the present invention greatly increases the efficiency for detecting the methylated CpG islands based on the high-throughput sequencing.

Figure 4:
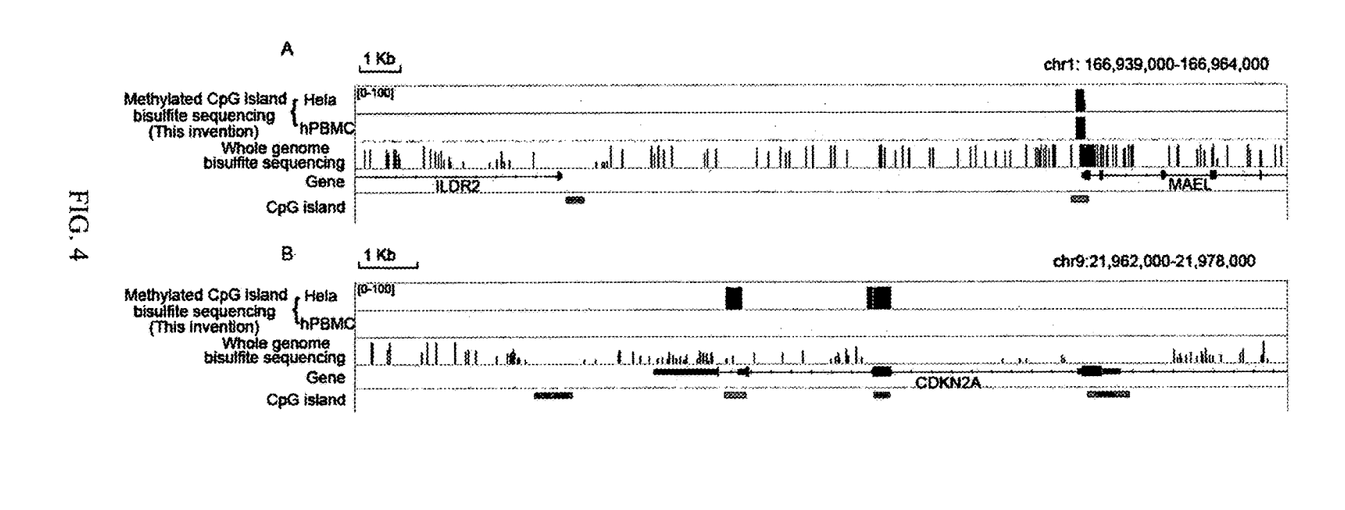
FIG. 4 IGV views of the present invention in comparison with the whole-genome bisulfite sequencing for the genomic regions containing MAEL, ILDR2 or CDKN2A.

FIG. 4 shows IGV views of the present invention in comparison with the whole-genome bisulfite sequencing for the genomic regions containing MAEL, ILDR2 or CDKN2A. FIG. 4A shows the genomic region containing MAEL and ILDR2. MAEL (maelstrom spermatogenic transposon silencer) is a gene specially expressed in the testis. The promoter CpG islands of this gene are demethylated in the germ cell while highly methylated in the somatic cell. On the contrary, the promoter CpG island of ILDR2 (immunoglobulin-like domain containing receptor 2) is demethylated in the somatic cell. For the genomic DNAs of both the HeLa cells and the hPBMCs, the promoter CpG island of MAEL is amplified by the present invention; the sequencing results shows that it is highly methylated in both genomes. In contrast, the promoter CpG island of ILDR2 is not amplified for both genomic DNAs. These results demonstrate that the present invention is able to selectively amplify the methylated CpG islands while does not amplify the demethylated CpG islands. The whole-genome bisulfite sequencing (of the human brain tissue) verifies that, in the normal somatic cell, the promoter CpG island of MAEL is highly methylated while that of MAEL is not methylated. On the other hand, it demonstrates that most isolated CpG sites are highly methylated, and they are selectively discarded during the process of the present invention for enriching the methylated CpG islands and establishing the library. FIG. 4B shows the genomic region containing CDKN2A (cyclin-dependent kinase inhibitor 2A). The CDKN2A genomic region contains several CpG islands being demethylated in the somatic cell while some of them are methylated in cancer cells. The present invention shows that 2 of 4 CpG islands are amplified in the genomic DNA of the HeLa cells and the sequencing results shows that they are highly methylated, while all 4 CpG islands are not amplified in the genomic DNA of the hPBMCs. These results further demonstrate that the present invention is able to accurately and high-efficiently enrich and amplify the methylated CpG islands for the high throughput sequencing.

Figure 5:
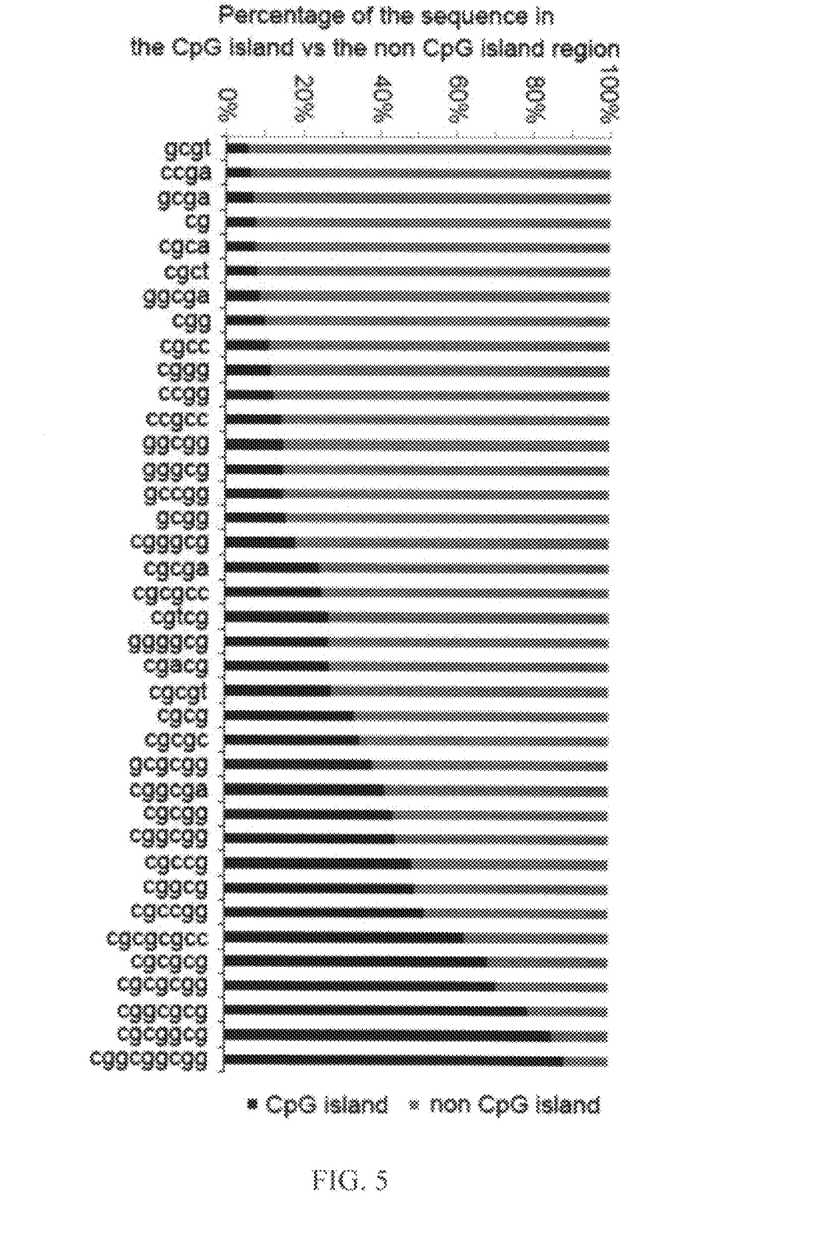
FIG. 5 The percentage of a number of short nucleotide sequences containing 1 to 3 CpG dinucleotides located within versus outside the CpG islands in the human genome.

FIG. 5 shows the bioinformatics analysis for the percentage of a number of short nucleotide sequences containing 1 to 3 CpG dinucleotides located within versus outside the CpG islands in the human genome. The results demonstrate that the enrichment of a short nucleotide sequence in the CpG islands is positively correlated with the number of CpG dinucleotide it contains.

TABLE 1

Data analysis of the present invention for the genomic DNAs of the HeLa cells and the hPBMCs.

|  | Raw data (reads (M)) | Raw data (Bases (Gb)) | Clean data (Reads (M)) | After adapter trimming (Reads (M)) | Uniquely mapped reads (Reads (M)) | Mapping efficiency | Reads overlapping the CpG islands (Reads (M)) | Percentage of reads overlapping the CpG islands | Enrichment of the CpG islands (observed/expected) | Number of CpG (depth >= 3) | Average sequencing depth for each CpG |
|---|---|---|---|---|---|---|---|---|---|---|---|
| HeLa | 12.9 | 1.3 | 7.5 | 6.4 | 3.6 | 57% | 1.4 | 39% | 56 | 495559 | 27× |
| hPBMC | 14.7 | 1.5 | 8.1 | 5.9 | 3.1 | 53% | 0.6 | 20% | 29 | 435131 | 21× |

Figure 6:
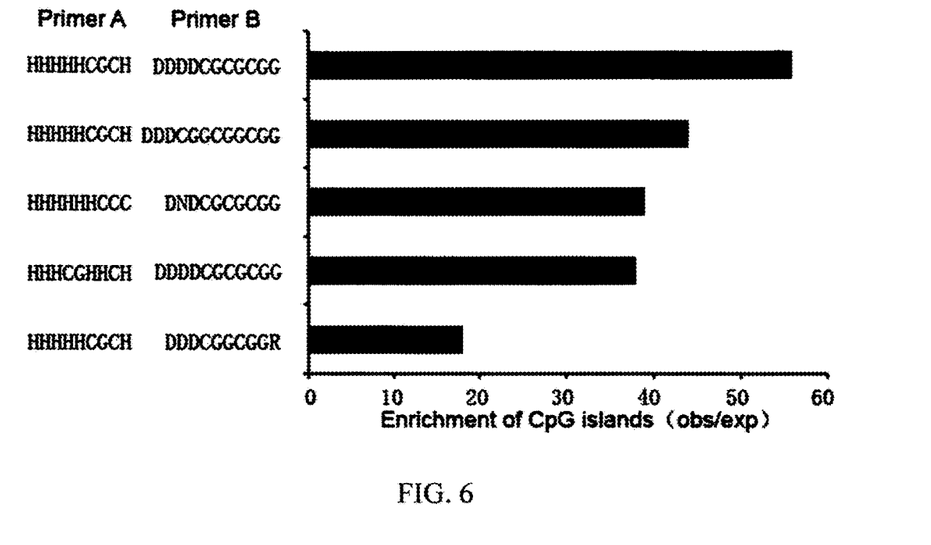
FIG. 6 Enrichment of the CpG islands by means of Primer A and Primer B with various 3' portion sequences.

FIG. 6 (SEQ ID NOS: 1, 2, 5-9) shows enrichment of the CpG islands by means of Primer A and Primer B with a variety of 3' portion sequences for the genomic DNA of the HeLa cells. The results show that the CpG islands enrichment is positively correlated to the CpG density of the primers. H=C/A/T/, D=G/A/T, R=G/A, N=A/T/C/G.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A high-throughput sequencing method for detecting methylated CpG islands comprising:
   (a) treating a DNA sample with a modifying agent to form the modified DNA wherein cytosine bases but not 5'-methyl-cytosine bases of the DNA sample are modified to uracil bases;
   (b) providing Primer A and DNA polymerase to the modified DNA to allow at least one round of linear amplification to form the semi-amplicon capable of anchoring Adapter Primer C at one end, wherein Primer A is composed of a 3' portion and a 5' portion, wherein the 3' portion contains 4 or more nucleotides capable of binding to the modified DNA and allowing amplification, wherein the 5' portion allows Adapter Primer C to bind to its reverse complementary sequence for PCR amplification;
   (c) amplifying the semi-amplicon by using Primer B and DNA polymerase to form the full-amplicon enriched with methylated CpG islands and capable of anchoring Adapter Primer C at one end and Adapter Primer D at the other end, wherein Primer B is composed of a 3' portion and a 5' portion, wherein the 3' portion contains 7 or more nucleotides and is a high-CpG-density sequence capable of binding to the semi-amplicon and allowing amplification and enrichment of the methylated CpG islands, wherein the high-CpG-density sequence is a sequence of which the 3'-terminal 7 nucleotides contain 2 or 3 CpG dinucleotides, wherein the 5' portion allows Adapter Primer D to bind to its reverse complementary sequence for PCR amplification;

(d) amplifying the full-amplicon by using Adapter Primer C, Adapter Primer D and DNA polymerase to form the final-amplicon via PCR exponential amplification;

(e) separating and purifying the final-amplicon to form the library for high-throughput sequencing, sequencing the library and analyzing the data.

2. The method according to claim 1, wherein a modifying agent is bisulfite.

3. The method according to claim 1, wherein the 3' portion of Primer A contains only C, A and T except for the CpG dinucleotide, wherein the 3' portion of Primer B contains only G, A and T except for the CpG dinucleotide.

4. The method according to claim 1, wherein the second nucleotide at the 3' terminal of Primer A is C.

5. The method according to claim 1, wherein the 3' portion of Primer A is a moderate-CpG-density sequence capable of binding to the modified DNA and allowing preliminary enrichment of methylated CpG islands, wherein the moderate-CpG-density sequence is a sequence of which the 3'-terminal 7 nucleotides contain 1 CpG dinucleotide.

6. The method according to claim 1, wherein the 3' portion of Primer A is a high-C-density sequence capable of binding to the modified DNA and allowing preliminary enrichment of methylated CpG islands, wherein the high-C-density sequence is a sequence of which the 3'-terminal 5 nucleotides contain 3 or more C,.

7. The method according to claim 1, wherein the 3' portion of Primer A is a high-CpG-density sequence capable of binding to the modified DNA and allowing preliminary enrichment of methylated CpG islands, wherein the high-CpG-density sequence is a sequence of which the 3'-terminal 7 nucleotides contain 2 or 3 CpG dinucleotides.

8. The method according to claim 1, wherein the 3' portion of Primer B is a high-GC-content sequence of which the 3'-terminal 10 nucleotides contain 7 or more C or G.

9. The method according to claim 1, wherein the 3' portion of Primer B is an extremely-high-CpG-density sequence of which the 3'-terminal 7 nucleotides contain 3 CpG dinucleotides.

10. The method according to claim 1, wherein the DNA polymerase in the step (b) is able to do strand displacement.

11. The method according to claim 1, wherein the DNA polymerase in the step (b) has deficiency in exonuclease activity.

12. The method according to claim 1, wherein 2~30 rounds of linear amplification are performed in the step (b).

13. The method according to claim 1, wherein the DNA polymerase in the step (c) is capable of hot-start.

14. A high-throughput sequencing method for detecting methylated CpG islands comprising:

(a) treating a DNA sample with a modifying agent to form the modified DNA wherein cytosine bases but not 5'-methyl-cytosine bases of the DNA sample are modified to uracil bases;

(b) providing Primer A and DNA polymerase to the modified DNA to allow at least one round of linear amplification to form the semi-amplicon enriched with methylated CpG islands and capable of anchoring Adapter Primer C at one end, wherein Primer A is composed of a 3' portion and a 5' portion, wherein the 3' portion is a high-CpG-density sequence capable of binding to the modified DNA and allowing amplification and enrichment of methylated CpG islands, wherein the high-CpG-density sequence is a sequence containing 7 or more nucleotides of which the 3'-terminal 7 nucleotides contain 2 or 3 CpG dinucleotides, wherein the 5' portion allows Adapter Primer C to bind to its reverse complementary sequence for PCR amplification;

(c) amplifying the semi-amplicon by using Primer B and DNA polymerase to form the full-amplicon enriched with methylated CpG islands and capable of anchoring Adapter Primer C at one end and Adapter Primer D at the other end, wherein Primer B is composed of a 3' portion and a 5' portion, wherein the 3' portion contains 4 or more nucleotides capable of binding to the semi-amplicon and allowing amplification, wherein the 5' portion allows Adapter Primer D to bind to its reverse complementary sequence for PCR amplification;

(d) amplifying the full-amplicon by using Adapter Primer C, Adapter Primer D and DNA polymerase to form the final-amplicon via PCR exponential amplification;

(e) separating and purifying the final-amplicon to form the library for high-throughput sequencing, sequencing the library and analyzing the data.

15. The method according to claim 14, wherein the DNA sample is derived from human cells, tissues, blood, body fluid, urine, excrement or their combination.

16. A kit for the high-throughput sequencing method for detecting methylated CpG islands comprising the Primer A, Primer B, Adapter Primer C, Adapter Primer D and DNA polymerase according to claim 14, as well as an instruction for the kit.

17. The method according to claim 1, wherein the sequences of the 5'-terminal 15 to 40 nucleotides of Prime A are the same as that of the 3'-terminal 15 to 40 nucleotides of Adapter Primer C, wherein the sequences of the 5'-terminal 15 to 40 nucleotides of Prime B are the same as that of the 3'-terminal 15 to 40 nucleotides of Adapter Primer D.

18. The method according to claim 1, wherein the DNA sample is derived from human cells, tissues, blood, body fluid, urine, excrement or their combination,.

19. A kit for the high-throughput sequencing method for detecting methylated CpG islands comprising the Primer A, Primer B, Adapter Primer C, Adapter Primer D and DNA polymerase according to claim 1, as well as an instruction for the kit.

20. The method according to claim 1, wherein the DNA sample is cell-free DNA in human plasma or serum.

* * * * *